United States Patent [19]
Laybourne et al.

[11] Patent Number: 5,470,511
[45] Date of Patent: Nov. 28, 1995

[54] VAPORIZER OVERFILL SAFETY DEVICE

[75] Inventors: John R. Laybourne, Wantage; Justin Mott, Didcot, both of United Kingdom

[73] Assignee: Blease Medical Equipment Limited, Chesham, United Kingdom

[21] Appl. No.: 259,610

[22] Filed: Jun. 14, 1994

[30] Foreign Application Priority Data

Jun. 14, 1993 [GB] United Kingdom ............... 9312250

[51] Int. Cl.$^6$ ................................ B01F 3/04
[52] U.S. Cl. ............... 261/55; 261/72.1; 128/204.13; 128/204.12
[58] Field of Search .............. 128/204.13, 203.12, 128/203.16, 203.17, 203.26, 203.27, 204.14, 203.25, 203.14; 261/DIG. 65, 72.1, 55

[56] References Cited

U.S. PATENT DOCUMENTS

| | | | |
|---|---|---|---|
| 2,915,061 | 12/1959 | Edmonson et al. | 128/203.13 |
| 3,483,866 | 12/1969 | Macintosh | 128/203.25 |
| 4,434,790 | 3/1984 | Olesen | 128/203.25 |
| 4,444,182 | 4/1984 | Gregory | 128/204.13 |
| 4,774,032 | 9/1988 | Coates et al. | 128/204.13 |
| 4,879,997 | 11/1989 | Bickford | 128/203.12 |
| 5,159,924 | 11/1992 | Cegielski et al. | 128/203.12 |

FOREIGN PATENT DOCUMENTS

| | | |
|---|---|---|
| 0049067 | 4/1982 | European Pat. Off. . |
| 1193241 | 5/1970 | United Kingdom . |
| 8606283 | 11/1986 | WIPO . |

*Primary Examiner*—Tim R. Miles
*Attorney, Agent, or Firm*—Fitch, Even, Tabin & Flannery

[57] ABSTRACT

A vaporizer comprises gas inlet and outlet ports, gas inlet and outlet control means, one or more liquid reservoir chambers, at least one gas passage, at least one gas vaporization zone, a liquid filler body including filler control means wherein there is communication between the gas inlet control means, gas outlet control means and filler control means such that i) when one or both of the gas inlet control means and gas outlet control means allows gas to flow into and/or out of the liquid reservoir chamber the filler control means will not allow liquid to pass either to or from the liquid reservoir chamber through the filler body, and ii) when one or both of the gas inlet control means and gas outlet control means allows gas to flow into and/or out of the liquid reservoir chamber the filler means cannot be moved to a position such that liquid could pass either to or from the liquid reservoir chamber through the filler body.

12 Claims, 7 Drawing Sheets

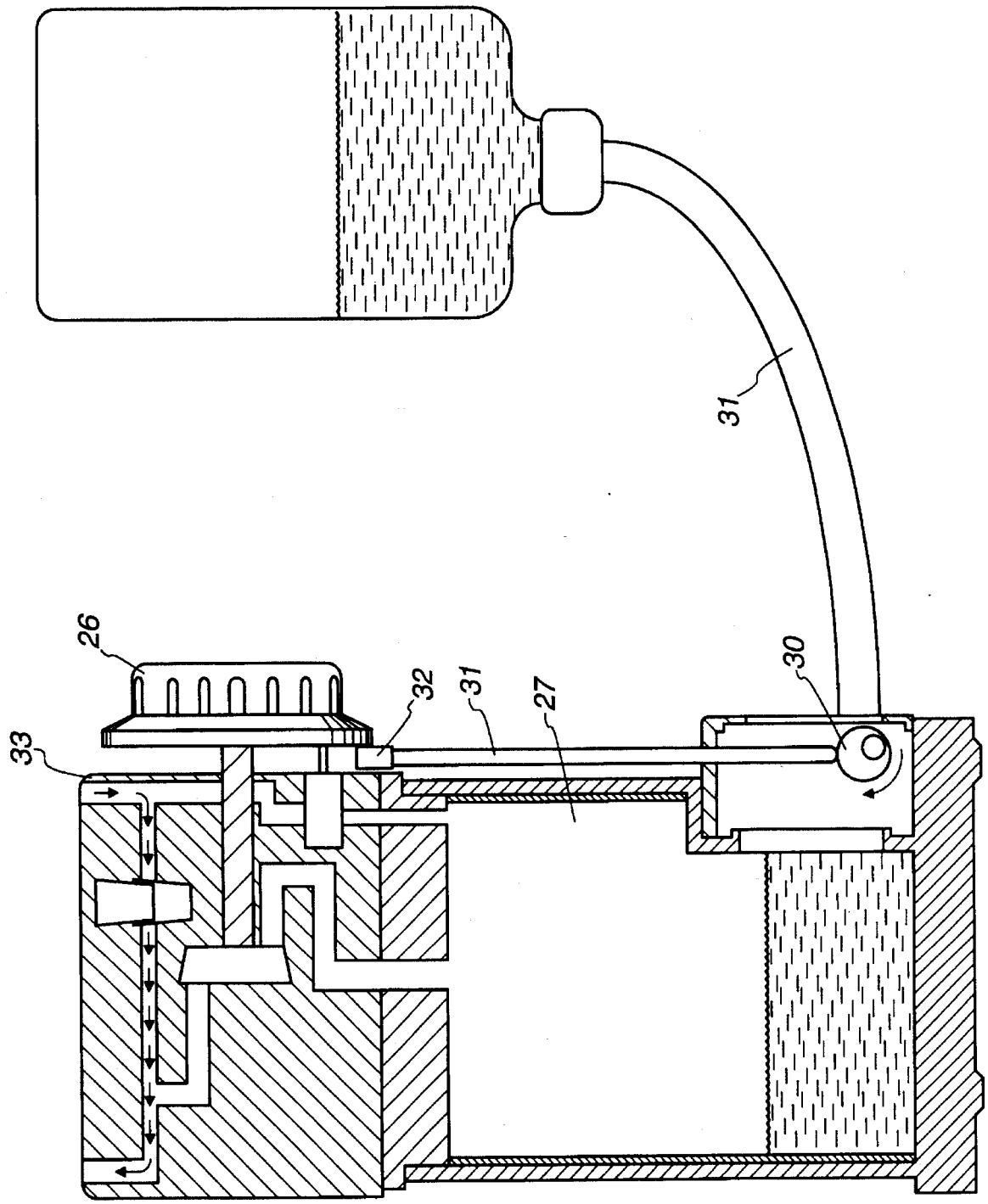

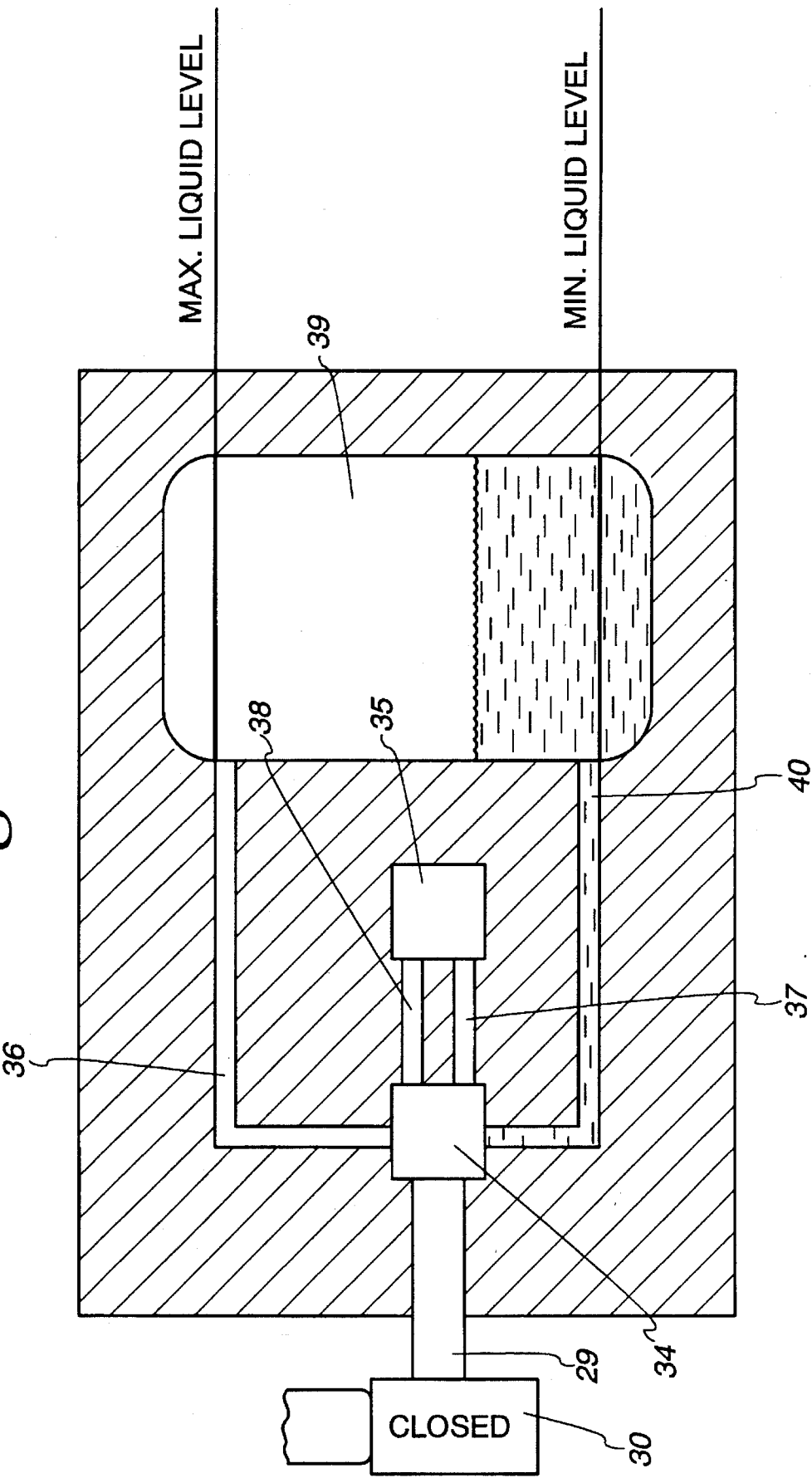

VAPORIZER OVERFILL SAFETY DEVICE

According to the present invention there is provided means to prevent the overfilling of vaporizers and in particular to prevent the filler means for said vaporizers being moved to an open operative position when carrier gas is able to pass into or out of the vaporizer.

The invention preferably applies to any vaporizer wherein the system is intended to be closed to external gas/atmosphere during filling of a liquid reservoir chamber in the vaporizer. For example when liquid is being inserted into a Plenum vaporizer the gas inlet and gas outlet ports are supposed to be closed and a source of replenishing liquid is sealably connected via a filler device to the filler body of the vaporizer. In this way liquid should only flow from the source into the liquid reservoir chamber if gas within said chamber is able to flow from said chamber into said source.

For ease of reference the invention is described with reference to a Plenum vaporizer. However, this is not intended to limit the invention which applies to any vaporizer system which is intended to be closed to external gas/atmosphere during filling. Plenum vaporizers are generally used as an integral part of anaesthetic machines and it is to this application that the present specification will be directed. However, it will be appreciated that the present invention applies equally to other usages.

Anaesthetic vaporizers are designed for "out of circuit use" (on the backbar of an anaesthetic machine), in continuous flow techniques of inhalation anaesthesia. Anaesthetic vaporizers convert the normally liquid anaesthetic agent into a vapour and allow the anaesthetist to determine the percentage of vapour being delivered in a controlled, predictable and safe way.

The anaesthetic machine is designed to deliver a controllable mixture of carrier gases (such as oxygen, nitrous oxide, air, carbon dioxide, helium etc.), into and through the vaporizer system or backbar. The backbar may be made up of more than one vaporizer and may also include an interlock system which stops more than one vaporizer being turned on at any one time. When the carrier gases pass through a vaporizer which has been switched on, the vaporizers task is to add the correct volume percentage (vol. %) of anaesthetic agent vapour to the carrier gas. The total gas flow, i.e carrier gas plus the vol. % of anaesthetic agent, then passes to the common gas outlet of the anaesthetic machine and thence through various devices to the patient.

Before describing the invention we will describe a known Plenum vaporizer. In FIG. 1 there is shown a schematic cross-section of a known plenum anaesthetic vaporizer. Carrier gas enters the vaporizer via inlet port 1. The carrier gas is split into two streams, by-pass stream 2 and inlet stream 3. The proportion of the carrier gas which comprises by-pass stream 2 is at least in part controlled by gas flow rate central means in the form of by-pass splitter valve 4 which as shown in FIG. 1 comprises a needle valve. Usually the greatest proportion of the carrier gas passes through the vaporizer as by-pass stream 2. Inlet stream 3 passes through an inlet control means in the form of a valve which as shown is a zero lock valve 5. Inlet stream 3 then continues into liquid reservoir chamber 6. In the device shown in FIG. 1 vaporization of the gas occurs within the liquid reservoir chamber. However, as will be seen in our co-pending United Kingdom Patent Application Number 9312212.5 filed on Jun. 14, 1993 and incorporated herein by reference, vaporization of the gas may occur in a gas vaporization zone substantially separate from the liquid reservoir chamber. The vapourized gas passes out of liquid reservoir chamber 6 via outlet control means 7 in the form of an adjustable valve. Outlet control valve 7 is controlled by control knob 8 and as shown in FIG. 1 comprises a neddle valve. The vapourized gas then mixes with by-pass stream 2 and exits the vaporizer via outlet port 9.

As shown in FIG. 1 there is also included a temperature compensator 10 which interacts with by-pass splitter valve 4 to control the proportion of gas split into by-pass stream 2 and inlet stream 3 respectively. The vaporizer further includes a filler body 11 which includes a liquid level indicator 12.

Whilst it is not shown in FIG. 1 vaporizers of the Plenum type generally utilise a keyed filling system. In such a system the filler body includes a keyed filler port into which a liquid filler source adaptor, usually a bottle adaptor, may be inserted. Leading from the keyed filler port are at least 2 passages which provide paths for fluid entry and gas exit to and from the liquid reservoir chamber respectively. In FIG. 1 these are shown as filler liquid passage 13 and filler gas passage 14 respectively. Filler means in the form of a valve is provided to open or close said passages. When opened the filler valve enables liquid to be transferred from a storage bottle or other source into the liquid reservoir chamber and gas to flow from said liquid reservoir chamber into said bottle.

Known vaporizers have inherent problems (i) relating to overfilling of the device and (ii) relating to accidental opening of the filler body valve whilst the vapour is in operation.

In at least one reported instance the filler valve was accidentally opened during a surgical operation, resulting in a large loss of anaesthetic vapour. The consequences of such large leaks include the exposure of the theatre personnel to anaesthetic vapours, loss of expensive anaesthetic agent, the possibility of anaesthesia becoming light, and damage to items on the anaesthetic table. The potential for disaster is great, including the possibility of personnel being sprayed with anaesthetic agent.

The overfilling problem occurs in the following circumstances amoungst others. The anaesthetic agent used to fill the liquid reservoir chamber of a vaporizer is generally stored in bottles. During filling of a vaporizer a bottle is attached to a bottle adaptor which generally includes a key which inserts into the filler body. The bottle adaptor may also include a fluid exit vein through which fluid may pass from the bottle into the filler body and thence into the liquid reservoir chamber. The bottle adaptor may also include a gas return vein through which gas may pass from the liquid reservoir chamber via the filler body into the bottle as liquid is dispelled therefrom. The filler body includes a filler liquid passage and a filler gas passage. These passages are designed so as to have air locks to prevent the fluid level rising any further than the designed limit when used correctly. When the designed level is attained, the filler gas passage becomes occluded by the higher liquid level and gas within the chamber has no exit from the chamber. However, if the control knob is set to a position other than the "off position", thereby allowing gas to pass, the liquid chamber can be vented into the fresh gas circuit of the rest of the anaesthetic machine. This presents a hazardous situation if the seal between the bottle and bottle adaptor is not gas tight, as the liquid level within the bottle can drop further due to a secondary inlet path of gas to the bottle and the liquid level within the vaporizer can continue to rise by-passing all of the safety passages by virture of the chamber no longer being a sealed container, allowing an overfill situation to occur.

It is the object of the present invention to provide a vaporizer which overcomes each of the above defficiencies.

According to the present invention there is provided a vaporizer comprising gas inlet and outlet ports, gas inlet and outlet control means, one or more liquid reservoir chambers, at least one gas passage, at least one gas vaporization zone, a liquid filler body including filler control means wherein there is communication between the gas inlet control means, gas outlet control means and filler control means such that i) when one or both of the gas inlet control means and gas outlet control means allows gas to flow into and/or out of the liquid reservoir chamber the filler control means will not allow liquid to pass either to or from the liquid reservoir chamber through the filler body, and ii) when one or both of the gas inlet control means and gas outlet control means allows gas to flow into and/or out of the liquid reservoir chamber the filler means cannot be moved to a position such that liquid could pass either to or from the liquid reservoir chamber through the filler body.

Gas inlet and outlet ports may be any type suitable to enable gas supply to be connected to the inlet port and gas take off to be connected to the outlet port. Their design will be dependant on the nature of the gas supply and take off members to be attached thereto.

Gas inlet control means and gas outlet control means may be any suitable means, examples of which include valves, zero lock ports, gates and the like. Preferably one or both of the gas inlet and outlet control means are adjustable such that the amount of gas entering and leaving the gas vaporization zone may be adjustable and so that the resistance or back pressure to flow entering the vaporization zone may be adjusted. One example of a valve is a needle valve. In one embodiment the gas inlet and outlet control means may be jointly controlled by one control such that at least adjustment between the open and closed positions will operate to affect both the gas inlet and outlet control means at the same time. Alternatively, the gas inlet and outlet control means may be interlinked so that they may be jointly and severally controlled, for example the gas outlet control means may be adjustable so as to change the flow of the gas passing it, but when moved to the closed position it interacts with the inlet control means so that both the outlet and inlet control means stop gas flowing into or out of the gas vaporization zone.

Vaporization of the gas occurs within one or more gas vaporization zones. In one embodiment at least a part of the vaporization of the gas takes place in the liquid reservoir chamber, as for example in previously known Plenum vaporizers. However, in our co-pending United Kingdom patent application number 9312212.5 filed on Jun. 14, 1993, there is disclosed a vaporizer wherein at least a part of the vaporization of the gas occurs within a gas vaporization zone at least partially separate from the liquid reservoir chamber which gas vaporization zone has a substantially constant volume notwithstanding changes in the liquid level in the liquid reservoir chamber during operation of the vaporizer. The disclosure in that application is incorporated herein by reference.

Wherein the vaporizer of the present invention is a Plenum vaporizer, it includes gas flow rate control means. The gas flow rate control means comprises means to control the ratio of the split of gas flow between the by-pass gas passage and the inlet gas passage, that is the dilution ratio. The gas flow rate control means may comprise a valve or other gas spliting device. In one embodiment the flow rate control means is provided by a by-pass splitting valve. In one form said valve is a needle valve. However, other known devices will be suitable. Preferably, the flow rate control means cooperates with a temperature compensator such that variations in temperature within the vaporizer will be detected by the temperature compensator which will act on the flow rate control means to adjust the flow rate such that as the temperature in the gas vaporization zone decreases the gas flow rate control means causes an increased proportion of the gas flow to be diverted into the gas vaporization zone.

The liquid reservoir chamber is preferably proximate the gas vaporization zone. The liquid reservoir chamber holds the liquid which throughout any single operation of the vaporizer will be vaporized and mixed with the carrier gas. The vaporizer includes a liquid filler body which is preferably located proximate the liquid reservoir chamber. Preferably the filler body includes filler control means to stop or allow, as the case may be, liquid to pass into the liquid reservoir chamber from a liquid replenishing source. The filler body preferably incorporates a keyed filler port. Preferably said keyed filler port is connected to the liquid reservoir chamber via at least one filler liquid passage and at least one filler gas exit passage such that as the level of liquid within the liquid reservoir chamber increases, the gas contained within the chamber exits via the filler gas passage and when the designed level of liquid is attained the gas outlet port will become occluded by the higher liquid level such that when the gas inlet and outlet control means are closed the gas within the chamber will have no exit from the liquid reservoir chamber. Preferably it further also incorporates a liquid level indicator.

The communication between the gas inlet control means, gas inlet control means and filler control means is provided by a mechanical device or an electrical device or a combination of both. In one embodiment it is provided by an interlock which interacts with both the filler control and the gas inlet and outlet control means.

It will be appreciated that if the gas inlet and outlet control means interact with each other such that movement of one to the closed position causes the other to be moved to a closed position then the interlock device need only communicate with that overall control. One part of the interlock device interacts with the filler control means such that when the filler control is in the open position, such that liquid could pass into or out of the liquid reservoir chamber through the filler body, the gas inlet and outlet control means are not permitted to be in any position other than a closed position in which gas cannot pass either into or out of the liquid reservoir chamber. Further, if either one or both of the gas inlet and outlet control means are in a position which would allow gas to pass either into or out of the liquid reservoir chamber then the interlock device prohibits the filler control means being moved to an open position such that liquid could pass into or out of the liquid reservoir chamber through the filler body.

The main chamber, other parts of the vaporizer in contact with anaesthetic liquid, and the mechanical interlock and cam may be made from stainless steel, Delrin (trade mark, a product of Du Pont) Brass to British standard 2874 standard CZ 132, anodized alluminium, or plastics which do not degrade when exposed to the liquid which is to be vaporized, and the like or any combination of these. The liquid absorbant material may be made of polytetra-fluoroethelene sold as TEFLON (trade mark) felt, cotton cloth felt, stainless woven mesh, polyethylene, porous plastics, scintered materials and the like or any combination of these.

BRIEF DESCRIPTION OF THE DRAWINGS

In FIG. 2b there is shown the same vaporizer and embodiment of the present invention as shown in FIG. 2a except that the gas inlet and outlet control means are now closed thereby prohibiting gas entering or exiting the liquid control chamber and the filler control means is open thereby allowing liquid to be passed into the liquid control chamber.

In FIG. 3a there is shown a schematic cross-section of one embodiment of the liquid filler body including the lower section of the interlock device of FIGS. 2a and 2b wherein the filler control means is in the closed position.

Figure 1:
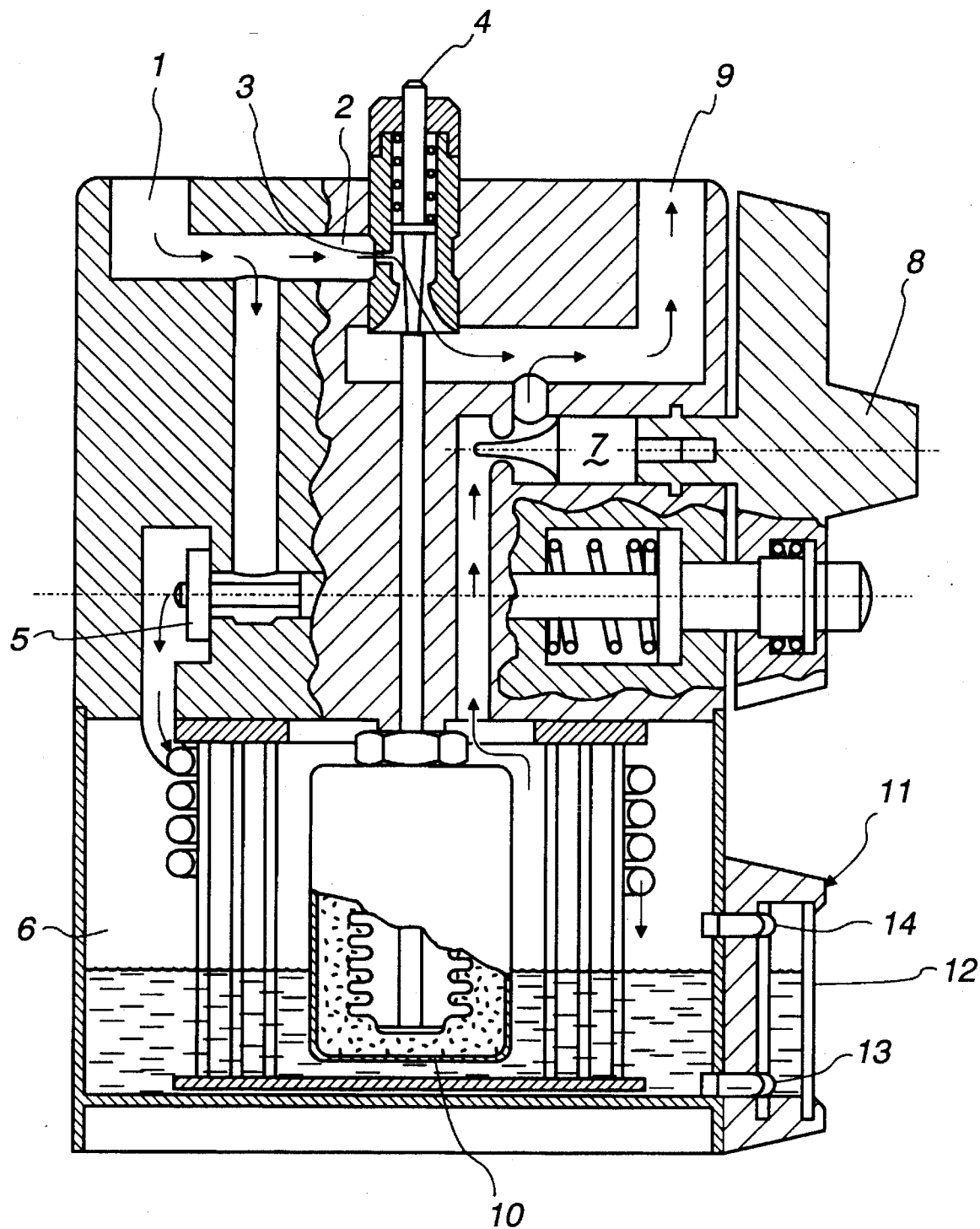
FIG. 1 shows a schematic cross-section of a known plenum anaesthetic vaporizer.
Figure 2A:
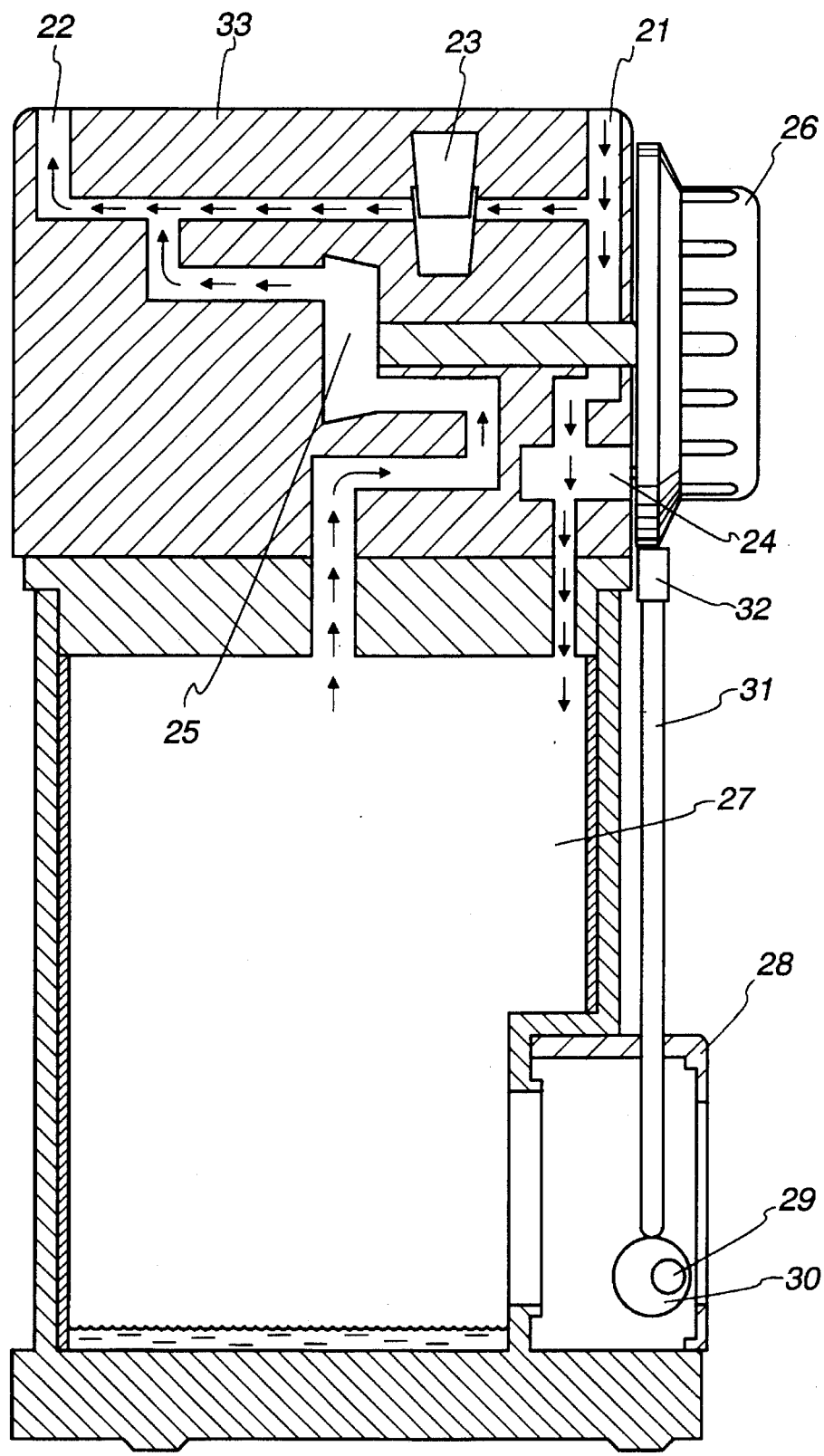
In FIG. 2a there is shown a vaporizer incorporating an interlock according to one embodiment of the present invention wherein the gas inlet and outlet control means are shown in the open position with gas passing into the liquid reservoir chamber and the filler control means in the closed position such that liquid and gas may not pass through the filler body.

The vaporizer shown in FIG. 2a incorporates inlet port 21 and outlet port 22, flow rate control means 23, gas inlet control means 24, gas outlet control means 25. Gas inlet control means 24 is a zero lock valve. Gas outlet control means 25 incorporates control knob 26 which is a depression switch. When control knob 26 is depressed the gas outlet control means allows gas to flow through it. The flow rate is adjustable by turning control knob 26. When control knob 26 is depressed, it also causes gas inlet control means 24 to open such that gas may pass through it to liquid reservoir chamber 27. When control knob 26 is not depressed, both gas inlet and outlet control means are closed such that gas cannot flow into or out of liquid reservoir chamber 27.

Located proximate liquid reservoir chamber 27 is filler body 28 which includes filler control means 29. Filler control means 29 includes cam 30 which forms part of the communication means between the filler control means and gas outlet and gas inlet control means 25 and 24. As shown in FIG. 2a the communication means comprises an interlock. The interlock further comprises arm 31 and foot 32.

As shown in FIG. 2a filler control means 29 is in the closed position and foot 32 is in position such that control knob 26 can be depressed. Further, foot 32 rests proximate control knob 26 such that if filler control means 29 is attempted to be opened, arm 31 will not move and therefore cam 30 cannot move thus stopping filler control means 29 being opened.

As shown in FIG. 2b control knob 26 is not depressed and the gas inlet and outlet control means are closed therefore gas cannot pass into or out of the liquid reservoir chamber 27. In this figure filler control means is open. The filler body incorporates a keyed filler port into which keyed filler device 31, which is connected to a bottle containing liquid to replenish the liquid reservoir chamber 27 may be inserted. As shown filler control means 29 is in the open position and cam 30 has caused arm 31 to be moved toward control knob 26, such that foot 32 is moved between the body of the vaporizer 33 and control knob 26, such that control knob 26 cannot be depressed and therefore gas inlet and outlet control means cannot be opened to allow gas to pass into or out of the liquid reservoir chamber 27.

As can be seen from FIG. 3a, when the filler control means 29 is in the closed position liquid cannot pass through keyed filler port 35 and gas cannot pass from the liquid reservoir chamber from filler gas passage 36. Filler valve 34 prohibits liquid flowing through liquid port passage 37. Filler valve 34 also prohibits gas passing through gas port passage 38. Also shown is liquid level indicator 39.

Figure 3B:
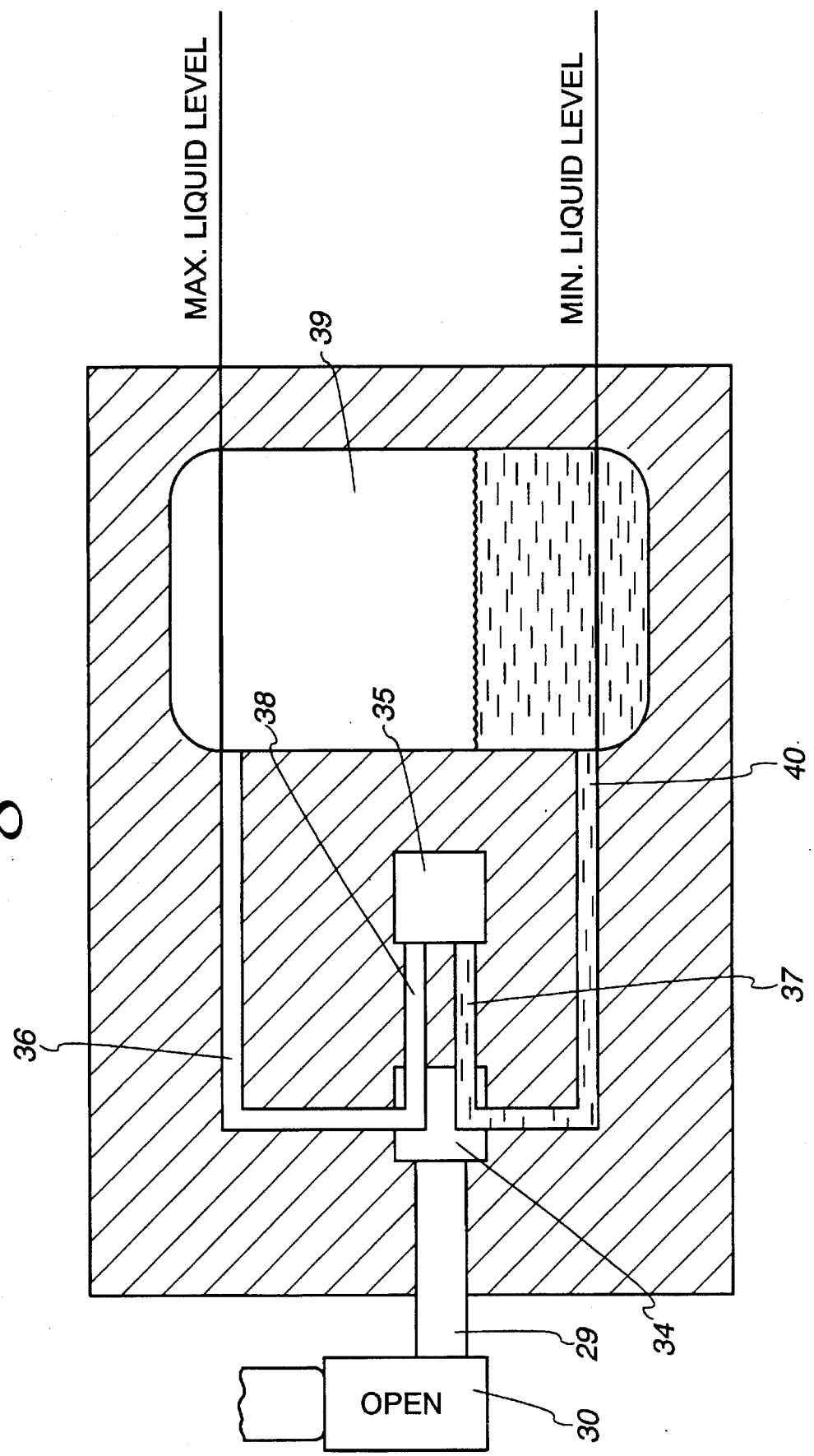
In FIG. 3b there is shown the liquid filler body of FIG. 3a wherein the filler control means is in the open position.

As shown in FIG. 3b filler control means 29 is in the open position and cam 30 has rotated such that arm 31 is moved toward control knob 26. Liquid passes from the keyed filler device in keyed filler port 35 through liquid port passage 37 via filler valve 34 into filler liquid passage 40 and into the liquid reservoir chamber. As liquid passes into the chamber, gas exits the chamber via filler gas passage 36 through filler control means 29, gas port passage 38 and out into the keyed filler device 31 and into the bottle. Thus, there is shown a closed system into which liquid cannot pass into the liquid reservoir chamber from the bottle containing the liquid unless gas passes from the liquid reservoir chamber 27 through the filler body, keyed filler device and into the bottle.

Figure 4A:
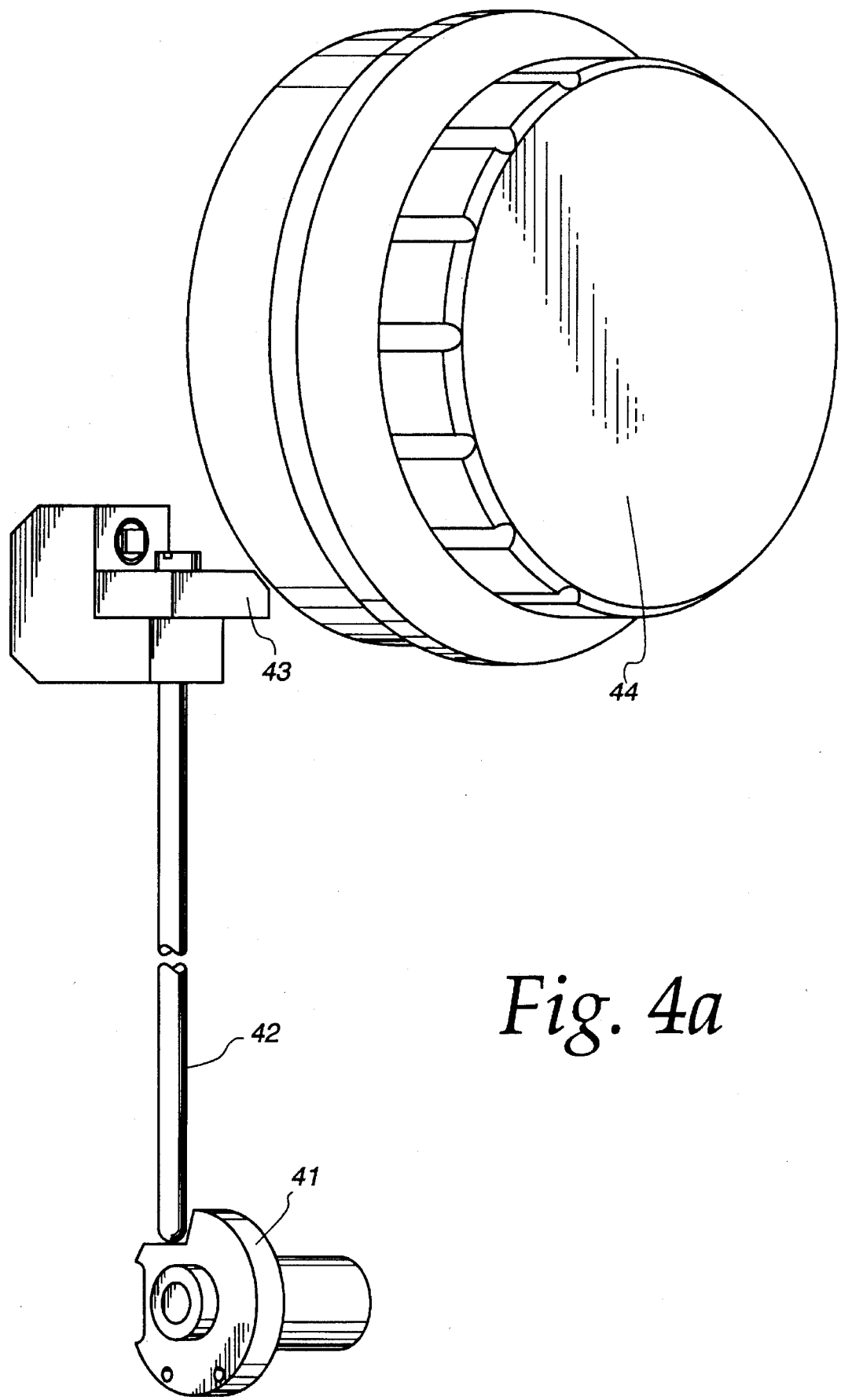
In FIG. 4a there is shown a different embodiment of an interlock device being one embodiment suitable for use in a vaporizer of the present invention wherein the filler control means is in the closed position.

In FIG. 4a there is shown a cam, arm, shoe and control knob from an interlock device similar to that depicted in FIGS. 2 and 3. The cam 41 is of a stepped design and arm 42 abuts one face of the cam. At the other end of arm 42 is located foot 43 which interacts with control knob 44 in the same manner as shown in FIG. 2.

Figure 4B:
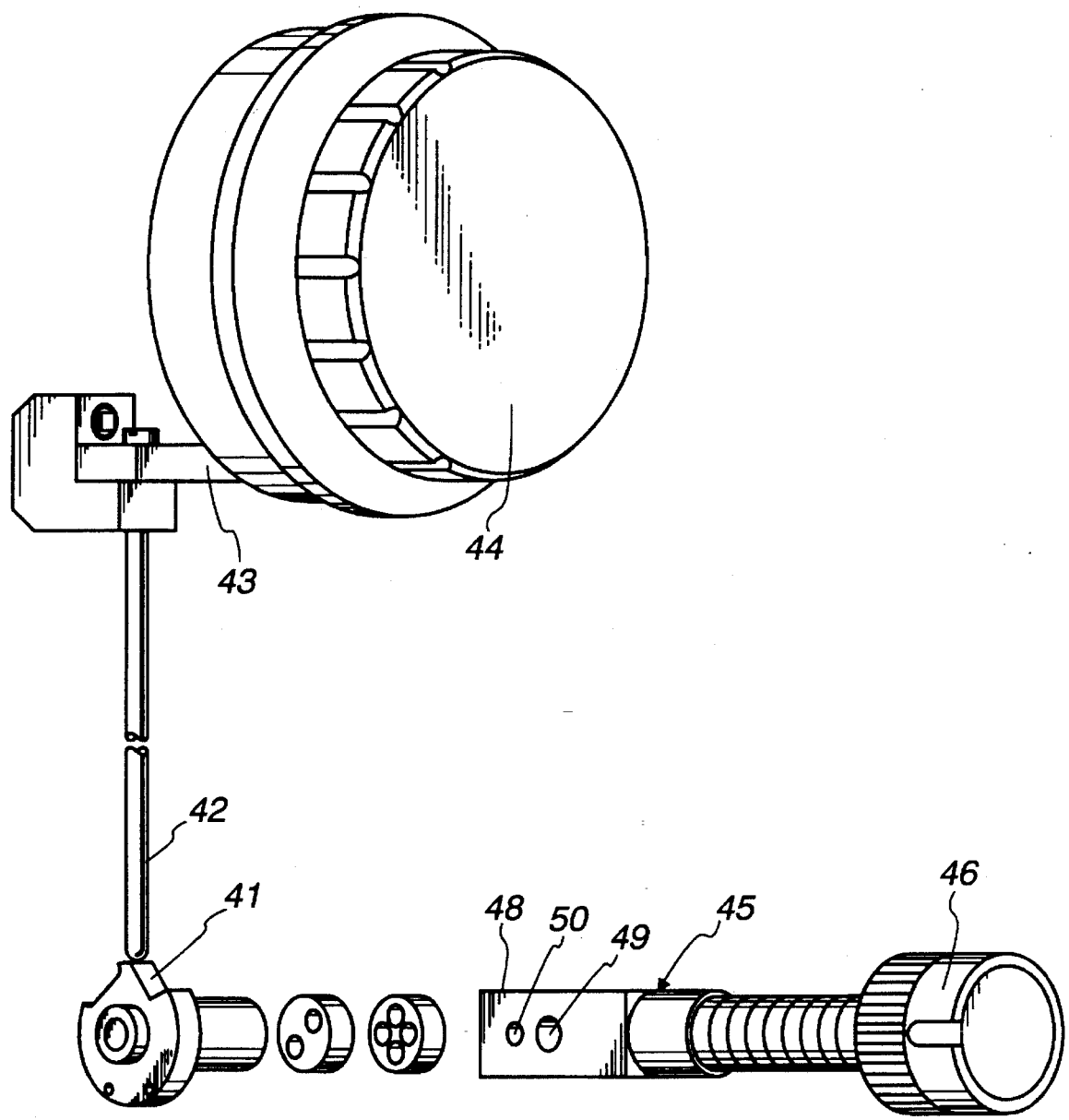
In FIG. 4b there is shown the interlock device depicted in FIG. 4a wherein the filler control is in the open position. There is also shown a representation of a keyed filler device and bottle attachment.

As can been seen in FIG. 4b the cam 41 has been rotated into the open position thus forcing arm 42 toward control knob 44 and foot 43 becomes located between control knob 44 and the body of the vaporizer (which is not shown). There is also shown keyed filler device 45 which includes bottle adaptor 46 and key 48. In the face of key 48 which faces the gas and liquid port passages (not shown) there is liquid mouth 49 and gas mouth 50. In use bottle adaptor 46 is connected to a bottle containing liquid. The liquid passes through keyed filler device 45 via liquid mouth 49 into the liquid port passage and when the filler means is open, into the liquid reservoir chamber and gas passes from the chamber via gas port passage through gas mouth 50 into the bottle attached to bottle adaptor 46. The two disc shaped objects located at the bottom of FIG. 4b of the drawing are two parts of the simple open/close valve. When in the open position, the two holes of the left-hand disc correspond with two holes of the right-hand disc which extend through the disc. The latter two holes correspond in position with apertures 49 and 50 of the keyed filler device. In other words, these two discs form part of the filler means but are not otherwise described in detail in this description. This is a standard type of valve, and one of ordinary skill in the art would comprehend the operation of such a valve.

We claim:

1. A vaporizer comprising gas inlet and outlet ports, gas inlet and outlet control means, one or more liquid reservoir chambers, at least one gas passage, at least one gas vaporization zone, a liquid filler body including filler control means wherein there is communication between the gas inlet control means, gas outlet control means and filler control means such that i) when one or both of the gas inlet control means and gas outlet control means allows gas to flow into and/or out of the liquid reservoir chamber the filler control means will not allow liquid to pass either to or from the liquid reservoir chamber through the filler body, and ii) when one or both of the gas inlet control means and gas outlet control means allows gas to flow into and/or out of the liquid reservoir chamber the filler means cannot be moved to a position such that liquid could pass either to or from the liquid reservoir chamber through the filler body.

2. A vaporizer as claimed in claim 1 wherein the interconnection is provided by electromechanical means.

3. A vaporizer as claimed in claim 1 wherein the communication is provided by an interlock extending between the filler control means and the gas inlet and outlet control means.

4. A vaporizer as claimed in claim 3 wherein the interlock is cam operated.

5. A vaporizer as claimed in claim 4 wherein the filler control means includes a valve rotatably operable between an open and a closed position, and a cam which operates the interlock.

6. A vaporizer as claimed in claim 5 wherein when the filler control means is rotated toward an open position such that liquid could pass to or from the liquid reservoir chamber through the filler body, the cam:
   i) will cause the interlock to move such that the gas inlet control means and gas outlet control means cannot be moved to a postion wherein gas can flow into and/or out of the liquid reservoir chamber, but
   ii) if the gas inlet and/or gas outlet control means are not closed but are in a position which would allow gas to pass into or out of the liquid reservoir chamber, the filler control means will be stopped by the interlock's interaction with the inlet and outlet control means from rotating, and hence the filler control means cannot be rotated to the open position, if either or both of the gas inlet control means and outlet control means are not closed.

7. A vaporizer as claimed in claim 1 wherein the gas inlet control means and gas outlet control means are interlinked such that one control knob operates both means to move them between open and closed positions and the communication is with that knob.

8. A vaporizer as claimed in claim 7 wherein said control knob is a "push-turn" member and wherein the gas inlet and outlet control means allow gas to flow into and/or out of the liquid reservoir chamber when said member is depressed but do not allow said gas to flow when the member is not depressed and the interlocked is stopped by the control knob moving when said member is depressed but is free to move when said member is not depressed.

9. A vaporizer as claimed in claim 7 wherein the control knob includes a recess such that when the gas inlet and outlet control means do not allow gas to flow into and/or out of the liquid reservoir chamber the interlock may move into and out of the recess thereby allowing the filler means to be opened but when the control knob is in any other position such that gas can flow into and/or out of the liquid reservoir chamber the interlock cannot move sufficiently such that the filler means may be opened.

10. A vaporizer as claimed in claim 7 wherein the filler control means includes a valve rotatably operable between an open and closed position and a cam which operates an interlock, said interlock extending between the filler control means and the gas inlet and outlet control means such that when the filler control means in rotated toward an open position such that liquid could pass to or from the liquid reservoir chamber through the filler body, the cam:
   i) will cause the interlock to move such that the gas inlet control means and gas outlet control means cannot be moved to a position wherein gas flows into and/or out of the liquid reservoir chamber, but
   ii) if the gas inlet and/or gas outlet control means are not closed but are in a position which would allow gas to pass into or out of the liquid reservoir chamber, the filler control means will be stopped by the interlock's interaction with the inlet and outlet control means from rotating, and hence the filler control means cannot be rotated to the open position, if either or both of the gas inlet control means and outlet control means are not closed.

11. A vaporizer as claimed in claim 10 wherein said control knob is a "push-turn" member and wherein the gas inlet and outlet control means allow gas to flow into and/or out of the liquid reservoir chamber when said member is depressed but do not allow said gas to flow when the member is not depressed and the interlock is stopped by the control knob moving when said member is depressed but is free to move when said member is not depressed.

12. A vaporizer as claimed in claim 10 wherein the control knob includes a recess such that when the gas inlet and outlet control means do not allow gas to flow into and/or out of the liquid reservoir chamber the interlock may move into and out of the recess thereby allowing the filler means to be opened but when the control knob is in any other position such that gas can flow into and/or out of the liquid reservoir chamber the interlock cannot move sufficiently such that the filler means may be opened.

\* \* \* \* \*